(12) United States Patent
Ellington et al.

(10) Patent No.: US 9,988,612 B2
(45) Date of Patent: Jun. 5, 2018

(54) T7 RNA POLYMERASE VARIANTS WITH EXPANDED SUBSTRATE RANGE AND ENHANCED TRANSCRIPTIONAL YIELD

(71) Applicant: THE BOARD OF REGENTS OF THE UNIVERSITY OF TEXAS SYSTEM, Austin, TX (US)

(72) Inventors: Andrew D. Ellington, Austin, TX (US); Adam J. Meyer, Austin, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days. days.

(21) Appl. No.: 15/127,617

(22) PCT Filed: Mar. 20, 2015

(86) PCT No.: PCT/US2015/021748
§ 371 (c)(1),
(2) Date: Sep. 20, 2016

(87) PCT Pub. No.: WO2015/143318
PCT Pub. Date: Sep. 24, 2015

(65) Prior Publication Data
US 2017/0211050 A1    Jul. 27, 2017

Related U.S. Application Data

(60) Provisional application No. 61/968,231, filed on Mar. 20, 2014.

(51) Int. Cl.
| | | |
|---|---|---|
| C12N 9/12 | (2006.01) |
| C12P 19/34 | (2006.01) |
| C12N 15/115 | (2010.01) |
| C12N 15/11 | (2006.01) |

(52) U.S. Cl.
CPC .......... *C12N 9/1247* (2013.01); *C12N 15/111* (2013.01); *C12N 15/115* (2013.01); *C12P 19/34* (2013.01); *C12Y 207/07006* (2013.01); *C12N 2310/16* (2013.01); *C12N 2320/51* (2013.01); *C12N 2330/00* (2013.01)

(58) Field of Classification Search
None
See application file for complete search history.

(56) References Cited

U.S. PATENT DOCUMENTS

| | | | |
|---|---|---|---|
| 7,507,457 B2 | 3/2009 | Mishima et al. | 428/64.1 |
| 7,507,567 B2 | 3/2009 | Suhiyama et al. | 435/194 |
| 8,105,813 B2 | 1/2012 | Diener et al. | 435/194 |
| 2011/0136181 A1 | 6/2011 | Oe et al. | 435/91.3 |

FOREIGN PATENT DOCUMENTS

WO    WO/14/028429    2/2014

OTHER PUBLICATIONS

Beaudry, et al., *Chem Biol.* 7:323-34, 2000.
Bershtein,S., et al., (2006) Robustness-epistasis link shapes the fitness landscape of a randomly drifting protein. Nature, 444, 929-32.
Bershtein,S., Goldin,K. and Tawfik,D.S. (2008) Intense neutral drifts yield robust and evolvable consensus proteins. J. Mol. Biol., 379, 1029-1044.
Brieba et al., "Roles of histidine 784 and tyrosine 639 in ribose discrimination by T7 RNA polymerase." *Biochemistry.* vol. 39, 2000, pp. 919-923.
Bryksin et al., *Biotechniques.* 48:463-5, 2010.
Burmeister, et al., *Chem Biol.* 12:25-33, 2005.
Cheetham et al., "Structure of a transcribing T7 RNA polymerase initiation complex." *Science.* vol. 286, 1999, pp. 2305-2309.
Chelliserrykattil et al., "Evolution of a T7 RNA polymerase variant that transcribes 2'-O-methyl RNA." *Nat Biotechnol.* vol. 22, 2004, pp. 1155-1160.
Dean et al., "Antisense oligonucleotide-based therapeutics for cancer." *Oncogene.* vol. 22, 2003, pp. 9087-9096.
Dickinson, et al., *Proc Natl Acad Sci USA.* 110(22):9007-12, 2013.
Ellefson, "Directed evolution of genetic parts and circuits by compartmentalized partnered replication." *Nat Biotechnol.* vol. 32, No. 1, 2014, pp. 97-101.
Ellington et al., "In vitro selection of RNA molecules that bind specific ligands." *Nature.* vol. 346, 1990, pp. 818-822.
Ge et al.(2010) Effects of chemical modification on the potency, serum stability, and immunostimulatory properties of short shRNAs. RNA, 16, 118-130.
Gibson, "Enzymatic assembly of overlapping DNA fragments." *Methods Enzymol.* vol. 498, 2011, pp. 349-361.
Goldsmith,M. and Tawfik,D.S. (2009) Potential role of phenotypic mutations in the evolution of protein expression and stability. *Proc. Natl. Acad. Sci. U.S.A.*, 106, 6197-202.
Guillerez, et al., *Proc Natl Acad Sci USA.* 102(17):5958-63, 2005.
Healy, et al., "Pharmacokinetics and biodistribution of novel aptamer compositions." *Pharm Res.* vol. 21, 2004, pp. 2234-2246.
Huang, et al., "Mechanism of ribose 2'-group discrimination by an RNA polymerase." *Biochemistry.* vol. 36, 1997, pp. 8231-8242.
Ibach, "Identification of a T7 RNA polymerase variant that permits the enzymatic synthesis of fully 2'-O-methyl-modified RNA." *J Biotechnol.* vol. 167, 2013, pp. 287-295.
International Preliminary Report on Patentability in International Application No. PCT/US2015/021748 dated Sep. 29, 2016.
International Search Report and Written Opinion in International Application No. PCT/US2015/021748 dated Jul. 2, 2015.
Jackson, et al., *RNA.* 12(7):1197-205, 2006.
Keefe et al., "SELEX with modified nucleotides." *Curr Opin Chem Biol.* vol. 12, 2008, pp. 448-456.
Knudsen, et al., "In vitro selection using modified or unnatural nucleotides." *Curr Protoc Nucleic Acid Chem.* Chapter 9, Unit 9.6, 2002.

(Continued)

*Primary Examiner* — Richard G Hutson
(74) *Attorney, Agent, or Firm* — Norton Rose Fulbright US LLP

(57) ABSTRACT

Disclosed are T7 RNA polymerase variants with enhanced transcriptional activity. T7 RNA polymerase variants are known which have the ability to incorporate modified ribonucleotides into growing RNA molecules. However, these variants have relatively low levels of transcriptional activity. Presented herein are mutations that increase the transcriptional activity of the variants with broad substrate range.

19 Claims, 11 Drawing Sheets

(56) References Cited

OTHER PUBLICATIONS

Kostyuk, et al., "Mutants of T7 RNA polymerase that are able to synthesize both RNA and DNA." *FEBS Lett.* vol. 369, 1995, pp. 165-168.

Kraynack et al., *RNA.* 12(1):163-76, 2006.

Layzer, *RNA.* 10:766-771, 2004.

Levin, et al., (2009) Following evolutionary paths to protein-protein interactions with high affinity and selectivity. Nat. Struct. Mol. Biol., 16, 1049-1055.

Lupold, et al., "Identification and characterization of nuclease-stabilized RNA molecules that bind human prostate cancer cells via the prostate-specific membrane antigen." *Cancer Res.* vol. 62, No. 14, 2002, pp. 4029-4033.

Majlessi, et al., *Nucleic Acids Res.* 26:2224-9, 1998.

Padilla et al., *Nucleic Acids Res.* 30:e138, 2002.

Protasevich,I.I. (1994) The studies of cooperative regions in T7 RNA polymerase. FEBS Lett., 349, 429-432.

Romero et al., *Nat Rev Mol Cell Biol.* 10:866-76, 2009.

Siegmund, et al., "Screening mutant libraries of T7 RNA polymerase for candidates with increased acceptance of 2'-modified nucleotides." *Chem Commun. (Camb).*, vol. 48, 2012, pp. 9870-9872.

Soskine,M. and Tawfik,D.S. (2010) Mutational effects and the evolution of new protein functions. Nat. Rev. Genet., 11, 572-582.

Sousa et al., *EMBO J.* 14:4609-21, 1995.

Stovall, et al., (2014) In Vitro Selection Using Modified or Unnatural Nucleotides. Curr. Protoc. Nucleic Acid Chem., 56, doi:10.1002/0471142700.nc0906s56.

Temiakov, et al., *Cell.* 116:381-91, 2004.

Tokuriki, et al., (2008) How protein stability and new functions trade off. PLoS Comput. Biol., 4,e1000002.

Van Nies, et al. "Unbiased tracking of the progression of mRNA and protein synthesis in bulk and in liposome-confined reactions." *ChemBioChem* vol. 14, 2013, pp. 1963-1966.

Wang, et al., "Evolution of an antibiotic resistance enzyme constrained by stability and activity trade-offs." *J Mol Biol.* vol. 320, 2002, pp. 85-95.

Waters, et al., *Blood.* 117:5514-22, 2011.

Wilson et al., "Building oligonucleotide therapeutics using non-natural chemistries." *Curr Opin Chem Biol.* vol. 10, 2006, pp. 607-614.

Boulain J-C. et al., Mutants with higher stability and specific activity from a single thermosensitive variant of T7 RNA polymerase. Protein Eng Des Sel, Sep. 4, 2013, vol. 26, No. 11, pp. 725-734.

Meyer A.J. et al., Transcription yield of fully 2'-modified RNA can be increased by the addition of thermostabilizing mutations to T7 RNA polymerase mutants. Nucleic Acids Res, Jul. 24, 2015, vol. 43, No. 15, pp. 7480-7488.

Search Report and Written Opinion issued in Singapore application No. 11201607720X dated Nov. 10, 2017.

FIG. 8 rGmH

FIG. 9

SEQUENCE LISTING

```
<160> NUMBER OF SEQ ID NOS: 3

<210> SEQ ID NO 1
<211> LENGTH: 883
<212> TYPE: PRT
<213> ORGANISM: Bacteriophage T7

<400> SEQUENCE: 1

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125
```

```
Ala Asp Asn Thr Thr Val Gln Ala Val Ala Ser Ala Ile Gly Arg Ala
130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
                180                 185                 190

Lys Gly Leu Leu Gly Gly Glu Ala Trp Ser Ser Trp His Lys Glu Asp
            195                 200                 205

Ser Ile His Val Gly Val Arg Cys Ile Glu Met Leu Ile Glu Ser Thr
        210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Tyr Trp Ala
        275                 280                 285

Asn Gly Arg Arg Pro Leu Ala Leu Val Arg Thr His Ser Lys Lys Ala
290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Leu Pro Met Lys Pro Glu Asp Ile Asp
        355                 360                 365

Met Asn Pro Glu Ala Leu Thr Ala Trp Lys Arg Ala Ala Ala Val
370                 375                 380

Tyr Arg Lys Thr Arg Leu Ala Ser Leu Ala Val Ser Ala Leu Ser Ser
385                 390                 395                 400

Cys Leu Ser Lys Pro Ile Ser Leu Leu Thr Ile Arg Pro Ser Gly Ser
                405                 410                 415

Leu Thr Thr Trp Thr Gly Ala Val Arg Val Tyr Ala Val Ser Met Phe
            420                 425                 430

Asn Pro Gln Gly Asn Asp Met Thr Lys Gly Arg Leu Thr Leu Ala Lys
                435                 440                 445

Gly Lys Pro Ile Gly Lys Glu Gly Tyr Tyr Trp Leu Lys Ile His Gly
            450                 455                 460

Ala Asn Cys Ala Gly Val Asp Lys Val Ser Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His Gly Leu Ser Tyr
            515                 520                 525

Asn Cys Ser Leu Pro Leu Ala Phe Asp Gly Ser Cys Ser Gly Ile Gln
530                 535                 540

His Phe Ser Ala Met Leu Arg Asp Glu Val Gly Gly Arg Ala Val Asn
```

```
                         545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
    610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 2
<211> LENGTH: 60
<212> TYPE: DNA
<213> ORGANISM: Artificial Sequence
<220> FEATURE:
<223> OTHER INFORMATION: Synthetic Primer

<400> SEQUENCE: 2
aatataatac gactcactat agaggagact gaaatggtga aggacgggtc cagtgcttcg        60

<210> SEQ ID NO 3
<211> LENGTH: 57
```

```
<212> TYPE: DNA
<213> ORGANISM: Artificial Sequence
<220> FEATURE:
<223> OTHER INFORMATION: Synthetic Primer

<400> SEQUENCE: 3
gaaaagacta gttacggagc tcacactcta ctcaacagtg ccgaagcact ggacccg      57
```

T7 RNA POLYMERASE VARIANTS WITH EXPANDED SUBSTRATE RANGE AND ENHANCED TRANSCRIPTIONAL YIELD

CROSS REFERENCE TO RELATED APPLICATIONS

This application is a national phase application under 35 U.S.C. § 371 of International Application No. PCT/US2015/021748, filed Mar. 20, 2015 which claims priority to U.S. Provisional Patent Application No. 61/968,231 filed Mar. 20, 2014. Both applications are hereby incorporated in their entirety.

GOVERNMENT SUPPORT

This invention was made with government support under Grant No. FA9550-10-1-0169 awarded by the Air Force Office of Scientific Research and Grant No. EB015403 awarded by the National Institutes of Health. The government has certain rights in the invention.

BACKGROUND OF THE INVENTION

A. Field of the Invention

The invention generally concerns the field of protein engineering. More particularly, disclosed herein are variants of T7 RNA polymerase with the ability to incorporate modified nucleotides and with enhanced transcriptional activity.

B. Description of Related Art

RNA is widely versatile and useful, but its chemical instability can render it unsuitable for many therapeutic and biotechnology functions. Oligonucleotides with altered chemistry, especially modifications of 2' position of the (deoxy)ribose have proven to be of great value (Wilson & Keefe, 2006). 2'-O-methyl RNA has a greater Tm, faster kinetics, and greater stability as antisense probes (Majlessi, et al., 1998) and siRNA with 2'F and 2'-O-methyl RNA have also proven to be more stable and target-specific (Layzer, 2004; Kraynack & baker, 2006; Jackson, et al., 2006; Dean & Bennet, 2003. Additionally, in vitro selection with 2' modified NTPs has yielded aptamers and ribozymes with greater stability and enhanced chemical potential (Healy, et al., 2004; Waters, et al., 2011; Lupold, et al., 2002; Keefe & Cload, 2008; Burmeister, et al., 2005; Beaudry, et al., 2000).

While modified RNA can be chemically synthesized it is often preferable to enzymatically produce it (especially for in vitro selection) (Ellington & Szostak, 1990). T7 RNA polymerase has long been utilized for the generation of RNA in vitro, and has previously been engineered and evolved to have an expanded substrate range. Most famously, the Y639F mutant allows for the polymerization of RNA transcripts contain nucleotides with 2'-Fluoro and 2'-amino modified ribose (Kostyuk, et al., 1995; Sousa & Padilla, 1995; Huang, et al., 1997). A further mutation, H784A, is thought to eliminate premature termination following the incorporation of a modified nucleotide, and the Y639F, H784A ("FA") double mutant can incorporate nucleotides with bulky modifications at the 2' position (e.g. 2'-O-methyl) (Padilla & Sousa, 2002; Brieba & Sousa, 2004).

A directed evolution approach, in which the aforementioned Y639 and H784 residues, as well as the important R425 and G542 were randomized, has been previously employed to create further T7 RNA polymerase variants with expanded substrate specificity (Chelliserrykattil & Ellington, 2004). The resulting library was enriched for T7 RNA polymerase variants that retained the ability to transcribe RNA in vivo (with natural ribose) and the screened for altered substrate specificities in vitro. A mutant, termed "RGVG," (R425, G542, Y639V, H784G plus additional E593G and V685A mutations that arose organically during the selection) showed strong activity with 2'-O-methyl UTP. A second mutant, termed "VRS," (G542V and H784S as well as the additional H772R mutation) was able to incorporate 2'-Fluoro modified pyrimidines. More recent works have also uncovered the "2P16" mutant (a version of RGVG with seven additional mutations (Siegmund, et al., 2012)) and the R425C mutant (Ibach, et al., 2013). Each of these mutants is reported to enable the creation of 2'-O-methyl RNA.

While the unique catalytic properties of these enzymes make them useful tools, several of them suffer from low activity, even with normal ribonucleotides. It has been proposed that mutations that confer new activity in an enzyme also destabilize the protein, rendering it less active overall, with low transcriptional yields (Wang, et al., 2002; Romero, et al., 2009).

SUMMARY OF THE INVENTION

The present application offers a solution to the current low activity problems associated with T7 RNA polymerase variants that are able to incorporate modified nucleotides. In certain aspects, disclosed are T7 RNA polymerase variants with mutations that can increase the activity of mutants that have expanded substrate range. The resulting polymerase mutants can be used to generate 2'-O-methyl modified RNA with yields much higher than enzymes currently employed.

Disclosed is a T7 RNA polymerase variant comprising: one or more substrate-broadening amino acid substitutions that confer an enhanced ability to incorporate 2'-modified mononucleotides compared to a wild-type T7 RNA polymerase; and one or more activity-enhancing amino acid substitutions that increase the transcriptional activity of the T7 polymerase variant relative to T7 polymerase variants without the activity-enhancing amino acid substitutions. In some embodiments, the one or more substrate-broadening amino acid substitutions comprise one or more of the following amino acid substitutions relative to the wild-type T7 RNA polymerase sequence of SEQ ID NO:1: G542V, E593G, Y639V, Y639F, V685A, H772R, H784A, H784S, and H784G. In some embodiments, the one or more substrate-broadening amino acid substitutions comprise G542V, H772R, and H784S. In some embodiments, the one or more substrate-broadening amino acid substitutions comprise Y639F. In some embodiments, the one or more substrate-broadening amino acid substitutions comprise Y639F and H784A. In some embodiments, the one or more substrate-broadening amino acid substitutions comprise E593G, Y639V, V685A, and H784G. In some embodiments, the 2'-modified mononucleotides that the T7 RNA polymerase variant is capable of incorporating into a growing RNA strand comprise one or more of 2'-fluoro CTP, 2'-fluoro UTP, 2'-fluoro ATP, 2'-fluoro GTP, 2'-amino CTP, 2'-amino UTP, 2'-amino ATP, 2'-O-methyl UTP, 2'-O-methyl ATP, 2'-O-methyl CTP, and 2'-O-methyl GTP. In some embodiments, the one or more activity-enhancing amino acid substitutions comprise one or more of the following amino acid substitutions: P266L, S430P, N433T, S633P, F849I, and F880Y. In some embodiments, the one or more activity-enhancing amino acid substitutions comprise two or more of the following amino acid substitutions: P266L, S430P, N433T, S633P, F849I, and F880Y. In some embodiments, the one or more activity-enhancing amino acid substitutions comprise S430P, N433T, S633P, F849I, and F880Y. In some embodiments, the one or more activity-enhancing amino acid substitutions comprise P266L, S430P, N433T, S633P, F849I, and F880Y. In some embodiments, the one or more activity-enhancing amino acid substitutions comprise P266L. In some embodiments, the one or more activity-enhancing amino acid substitutions comprise S633P and F849I. In some embodiments, the one or more activity-enhancing amino acid substitutions comprise S633P and F880Y. In some embodiments, the one or more activity-enhancing amino acid substitutions comprise F849I and F880Y. In some embodiments, the one or more activity-enhancing amino acid substitutions comprise S633P, F849I, and F880Y.

Also disclosed is a T7 RNA polymerase variant comprising the following amino acid substitutions: N433T, E593G, Y639V, V685A, H784G, S430P, S633P, F849I, and F880Y.

Also disclosed is a nucleic acid molecule encoding any of the T7 RNA polymerase variants described above. Also disclosed is an expression vector comprising a nucleic acid sequence encoding any of the T7 RNA polymerase variants described above. Also disclosed is an isolated cell transformed with such an expression vector, wherein the transformed cell is capable of expressing any of the T7 RNA polymerase variants described above.

Also disclosed is a reaction mixture comprising any of the T7 RNA polymerase variants described above, a DNA template comprising a T7 RNA polymerase promoter, and one or more 2'-modified mononucleotides. In some embodiments, the one or more 2'-modified mononucleotides comprise one or more of 2'-fluoro CTP, 2'-fluoro UTP, 2'-fluoro ATP, 2'-fluoro GTP, 2'-amino CTP, 2'-amino UTP, 2'-amino ATP, 2'-O-methyl UTP, 2'-O-methyl ATP, 2'-O-methyl CTP, and 2'-O-methyl GTP. Also disclosed is a method of making an RNA polynucleotide comprising one or more 2'-modified mononucleotides, the method comprising incubating the reaction mixture described above at 37° C. In some embodiments, the RNA polynucleotide is an aptamer. In some embodiments, the RNA polynucleotide is nuclease resistant. Also disclosed is a method of making a therapeutic RNA polynucleotide comprising one or more 2'-modified mononucleotides, the method comprising incubating the reaction mixture described above at 37° C., wherein the DNA template further comprises a template sequence complementary to the therapeutic RNA polynucleotide. In some embodiments, the therapeutic RNA polynucleotide is an miRNA or pre-miRNA. In some embodiments, the therapeutic RNA polynucleotide is an aptamer. In some embodiments, the one or more 2'-modified mononucleotides comprises one or more of 2'-fluoro CTP, 2'-fluoro UTP, 2'-fluoro ATP, and 2'-fluoro GTP. In some embodiments, the nucleotide sequence of the therapeutic RNA polynucleotide is complementary to a portion of the sequence of a target gene mRNA. In some embodiments, the one or more 2' modified mononucleotides comprises one or more of 2'-O-methyl UTP, 2'-O-methyl ATP, 2'-O-methyl GTP, and 2'-O-methyl CTP. In some embodiments, the therapeutic RNA polynucleotide is nuclease resistant. Also disclosed is a method of making an RNA polynucleotide probe comprising one or more 2'-modified mononucleotides, the method comprising incubating the reaction mixture described above at 37° C., wherein the DNA template further comprises a template sequence complementary to the RNA polynucleotide probe. In some embodiments, the one or more 2' modified mononucleotides comprises one or more of 2'-O-methyl UTP, 2'-O-methyl ATP, 2'-O-methyl GTP, and 2'-O-methyl CTP.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, the methods and systems of the present invention that "comprises," "has," "includes" or "contains" one or more elements possesses those one or more elements, but is not limited to possessing only those one or more elements. Likewise, an element of a method or system of the present invention that "comprises," "has," "includes" or "contains" one or more features possesses those one or more features, but is not limited to possessing only those one or more features.

The feature or features of one embodiment may be applied to other embodiments, even though not described or illustrated, unless expressly prohibited by this disclosure or the nature of the embodiments.

Any method or system of the present invention can consist of or consist essentially of—rather than comprise/include/contain/have—any of the described elements and/or features and/or steps. Thus, in any of the claims, the term "consisting of" or "consisting essentially of" can be substituted for any of the open-ended linking verbs recited above, in order to change the scope of a given claim from what it would otherwise be using the open-ended linking verb.

Details associated with the embodiments described above and others are presented below.

BRIEF DESCRIPTION OF THE DRAWINGS

Figures 4A, 4B, 4C:
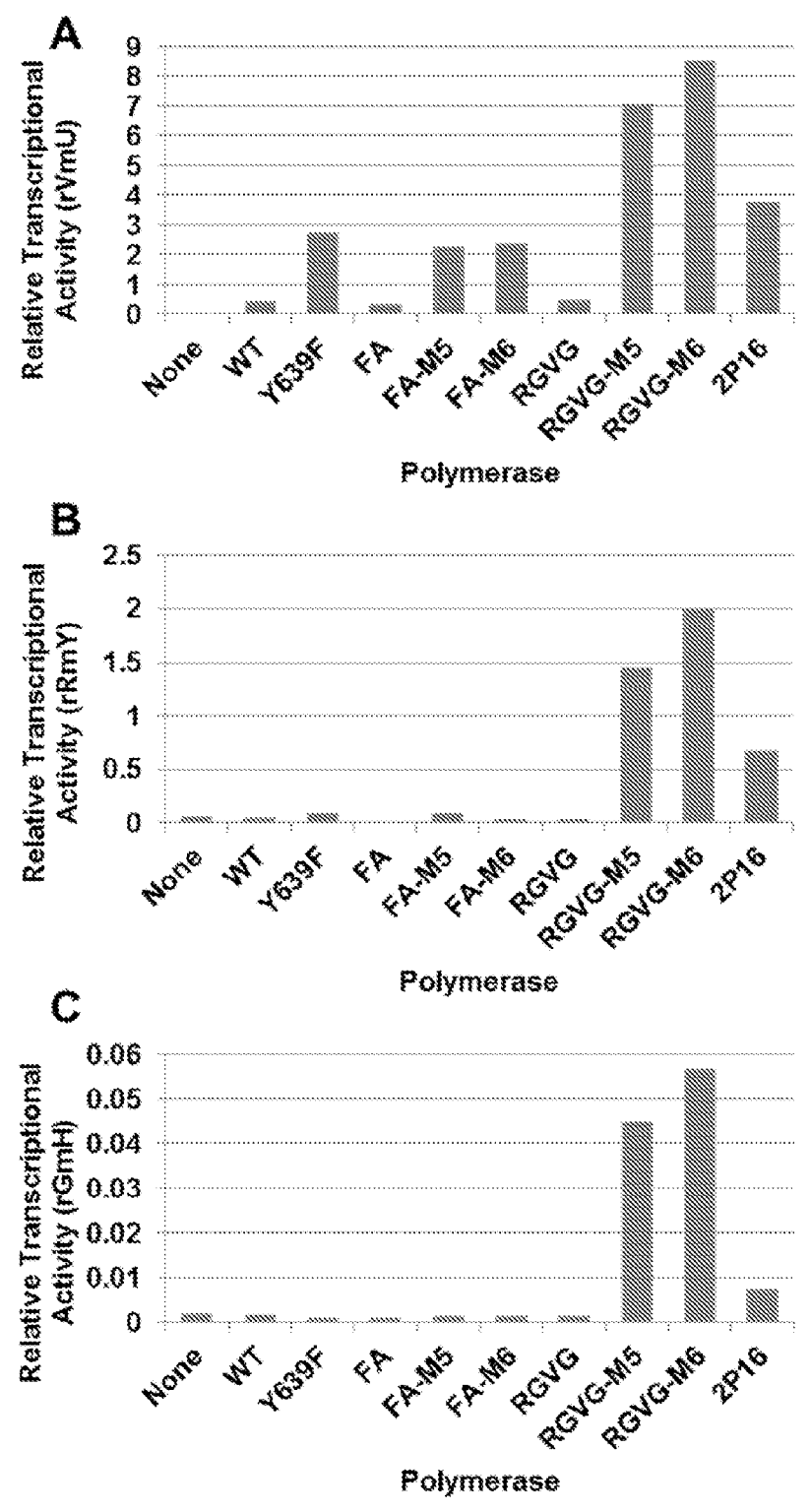

FIGS. 4A-4C. Stabilized T7 RNA polymerase mutants have increased yield of heavily modified RNAs. Transcription assay for incorporation of 2'-O-methyluridine (rVmU, A), 2'-O-methylpyrimidines (rRmY, B), or 2'-O-methyladenosine and 2'-O-methylpyrimidines (rGmH, C). Transcripts were labelled by inclusion of ($\alpha^{32}$P)ATP (rVmU and rRmY) or ($\alpha^{32}$P)GTP (rGmH) and analyzed by denaturing PAGE. All values are normalized to 100, representing the yield of WT T7 RNA polymerase with ribonucleotides (rN). Transcriptions ran four hours (rVmU and rRmY) or 20 hours (rGmH).

FIG. 7. Transcription assay for incorporation of 2'-O-methyluridine (rVmU). Transcripts were labelled by inclusion of ($\alpha^{32}$P)ATP and analyzed by denaturing PAGE. Transcriptions ran four hours. A reaction containing WT T7 RNA polymerase with ribonucleotides (rN) is shown for comparison.

FIG. 8. Transcription assay for incorporation of 2'-O-methylpyrimidines (rRmY). Transcripts were labelled by inclusion of ($\alpha^{32}$P)ATP and analyzed by denaturing PAGE. Transcriptions ran four hours. A reaction containing WT T7 RNA polymerase with ribonucleotides (rN) is shown for comparison.

FIG. 9. Transcription assay for incorporation of 2'-O-methyladenosine and 2'-O-methylpyrimidines (rGmH). Transcripts were labelled by inclusion of ($\alpha^{32}$P)GTP and analyzed by denaturing PAGE. Transcriptions ran 20 hours. A reaction (diluted 50-fold) containing WT T7 RNA polymerase with ribonucleotides (rN) is shown for comparison.

DETAILED DESCRIPTION OF THE INVENTION

Figures 1A, 1B, 1C, 1D:
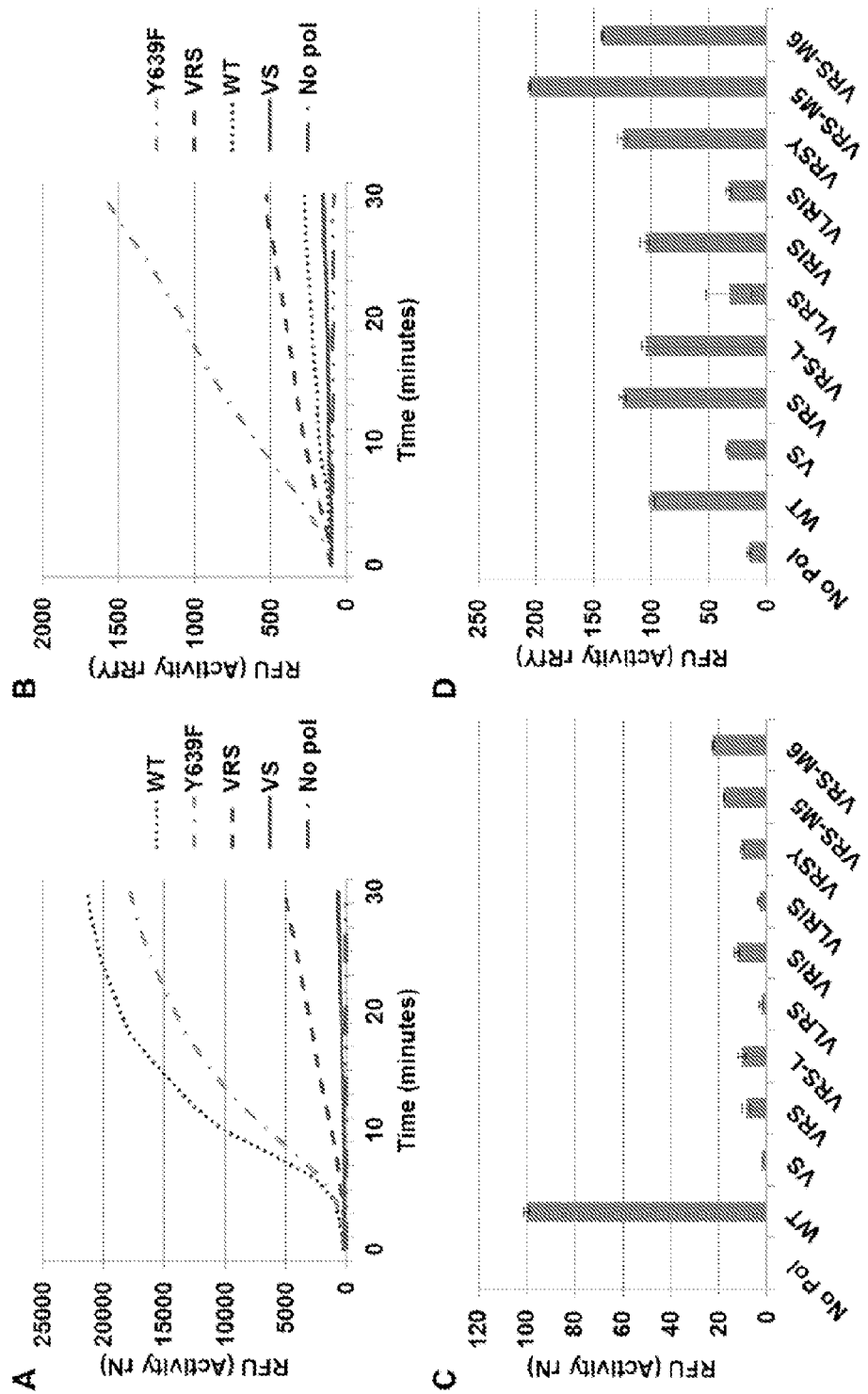
FIGS. 1A-1D. Stabilizing mutations increase the activity of the VRS mutant. A) Real time measurement of ribonucleotide (rN) transcriptional output. B) Real time measurement of 2'-fluoropyrimidine (rRfY) transcriptional output. C) Measurement of ribonucleotide (rN) transcriptional output after three hours. D) Measurement of 2'-fluoropyrimidine (rRfY) transcriptional output after three hours. Fluorescent readings (in Relative Fluorescent Units, RFU) indicate the presence of the fluorescent aptamer, spinach. Error bars represent standard error resulting from 3 independently assembled reactions.

Various features and advantageous details are explained more fully with reference to the non-limiting embodiments that are illustrated in the accompanying drawings and detailed in the following description. It should be understood, however, that the detailed description and the specific examples, while indicating embodiments of the invention, are given by way of illustration only, and not by way of limitation. Various substitutions, modifications, additions, and/or rearrangements will become apparent to those of ordinary skill in the art from this disclosure.

In the following description, numerous specific details are provided to provide a thorough understanding of the disclosed embodiments. One of ordinary skill in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

A. T7 RNA POLYMERASE

The wild type T7 RNA polymerase has the following sequence (SEQ ID NO: 1):

MNTINIAKNDFSDIELAAIPFNTLADHYGERLAREQLALEHESYEMGEAR

FRKMFERQLKAGEVADNAAAKPLITTLLPKMIARINDWFEEVKAKRGKRP

TAFQFLQEIKPEAVAYITIKTTLACLTSADNTTVQAVASAIGRAIEDEAR

FGRIRDLEAKHFKKNVEEQLNKRVGHVYKKAFMQVVEADMLSKGLLGGEA

WSSWHKEDSIHVGVRCIEMLIESTGMVSLHRQNAGVVGQDSETIELAPEY

AEAIATRAGALAGISPMFQPCVVPPKPWTGITGGGYWANGRRPLALVRTH

SKKALMRYEDVYMPEVYKAINIAQNTAWKINKKVLAVANVITKWKHCPVE

DIPAIEREELPMKPEDIDMNPEALTAWKRAAAAVYRKTRLASLAVSALSS

CLSKPISLLTIRPSGSLTTWTGAVRVYAVSMFNPQGNDMTKGRLTLAKGK

PIGKEGYYWLKIHGANCAGVDKVSFPERIKFIEENHENIMACAKSPLENT

WWAEQDSPFCFLAFCFEYAGVQHHGLSYNCSLPLAFDGSCSGIQHFSAML

RDEVGGRAVNLLPSETVQDIYGIVAKKVNEILQADAINGTDNEVVTVTDE

NTGEISEKVKLGTKALAGQWLAYGVTRSVTKRSVMTLAYGSKEFGFRQQV

LEDTIQPAIDSGKGLMFTQPNQAAGYMAKLIWESVSVTVVAAVEAMNWLK

SAAKLLAAEVKDKKTGEILRKRCAVHWVTPDGFPVWQEYKKPIQTRLNLM

FLGQFRLQPTINTNKDSEIDAHKQESGIAPNFVHSQDGSHLRKTVVWAHE

KYGIESFALIHDSFGTIPADAANLFKAVRETMVDTYESCDVLADFYDQFA

DQLHESQLDKMPALPAKGNLNLRDILESDFAFA

B. EXAMPLES

The present invention will be described in greater detail by way of specific examples. The following examples are offered for illustrative purposes only, and are not intended to limit the invention in any manner. Those of skill in the art will readily recognize a variety of noncritical parameters which can be changed or modified to yield essentially the same results.

Example 1

Materials and Methods

Preparation of T7 RNA Polymerase Variants

The T7 RNA polymerase ORF was cloned into pQE-80L (Qiagen). All T7 RNA polymerase variants were derived from this plasmid either by Mega-primer PCR (Bryksin & Matsumura, 2010) or Isothermal assembly (Gibson, 2011). Plasmids were transformed into BL21-gold (Agilent) E. coli cells. Cells were grown in 2×YT media at 37° C. overnight. Subcultures were grown at 37° C. until reaching OD600 ~0.7-0.8 at which point 1 mM IPTG was added. Cells were grown four hours at 37° C., pelleted, and frozen at −80'C. Pellets were resuspended in binding buffer (50 mM Tris-Hcl, pH8.0, 0.5 M NaCl, 5 mM imidazole). Resuspended cells were lysed via sonication on ice using 50% probe amplitude for 3 minutes (1s ON, 1s OFF). Cell debris was pelleted by centrifugation (30 min: 10,000 g). His-tagged T7 RNA polymerase was purified by immobilized metal affinity chromatography (IMAC). The lysate was run over 1 ml (bead volume) Ni-NTA (Fisher) gravity column pre-equilibrated with binding buffer. The column was washed with 10 column volumes of wash buffer (50 mM Tris-Hcl, pH 8.0, 0.5 M NaCl, 20 mM imidazole). T7 RNA polymerase was eluted off the column by the addition of 3 column volumes of elution buffer (50 mM Tris-Hcl, pH 8.0, 0.5 M NaCl, 250 mM imidazole). Dialysis was performed in final storage buffer (50 mM Tris-Hcl, pH 8.0, 100 mM NaCl, 1 mM DDT, 1 mM EDTA). Dialates were adjusted to 1 mg/ml and added to an equal volume of glycerol (final concentration 0.5 mg/ml).

In Vitro Transcription Assays

Real-time transcription reactions (FIG. 1, FIGS. 3A-3B) contained 40 mM Tris-HCl pH 8.0, 30 mM MgCl2, 6 mM spermadine, 6 mM each NTP (or modified NTP), 10 mM DTT, 500 mM T7 RNA polymerase, 500 mM DNA template, and 0.17 mg/ml DFHBI (in DMSO). Reactions were incubated for up to 4 hours at 37° C. with spinach fluorescence (Excitation/Emission 469/501) reading taken one to four minutes in a Safire monochromator (Tecan). Spinach templates were made by thermal cycling overlapping primers (5'-AATATAATACGACTCACTATAGAGGAGACT-GAAATGGTGAAGGACGGGTCCAGT GCTTCG (SEQ ID NO: 2) and 5'-GAAAAGACTAGTTACGGAGCTCA-CACTCTACTCAACAGTGCCGAAGCACTGGAC CCG (SEQ ID NO: 3)) with Accuprime Pfx in its standard buffer (94° C.: 2 min, 12 cycles [94° C.: 15 s, 50° C.: 30 s, 68° C.: 30 s], 68° C.: 1 min). Templates were purified by QIAquick Gel Extraction Kit (Qiagen).

Figure 6:
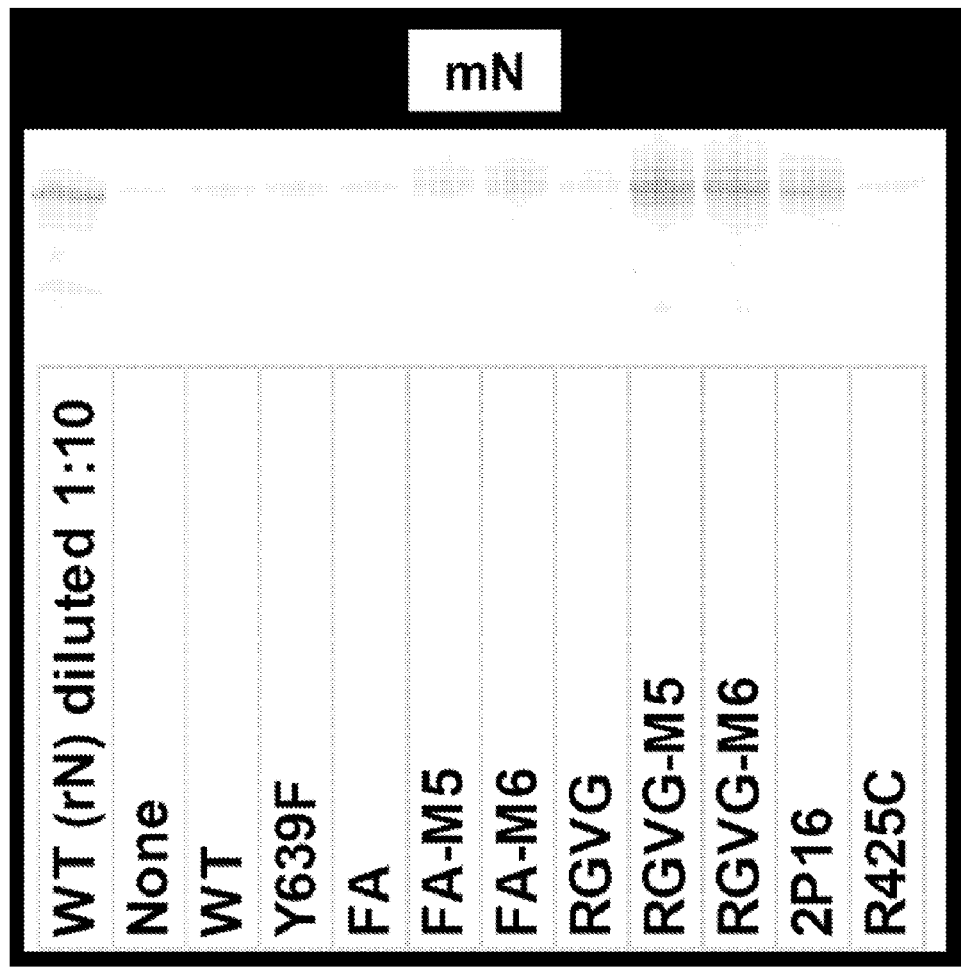
FIG. 6. Transcription assay for incorporation of 2'-O-methylnucleotides (mN) in a permissive buffer. Transcripts were analyzed by denaturing PAGE and imaged after staining in SYBR-Gold. Transcriptions ran 20 hours. A reaction (diluted 10-fold) containing WT T7 RNA polymerase with ribonucleotides (rN) is shown for comparison.
Figures 7, 8:
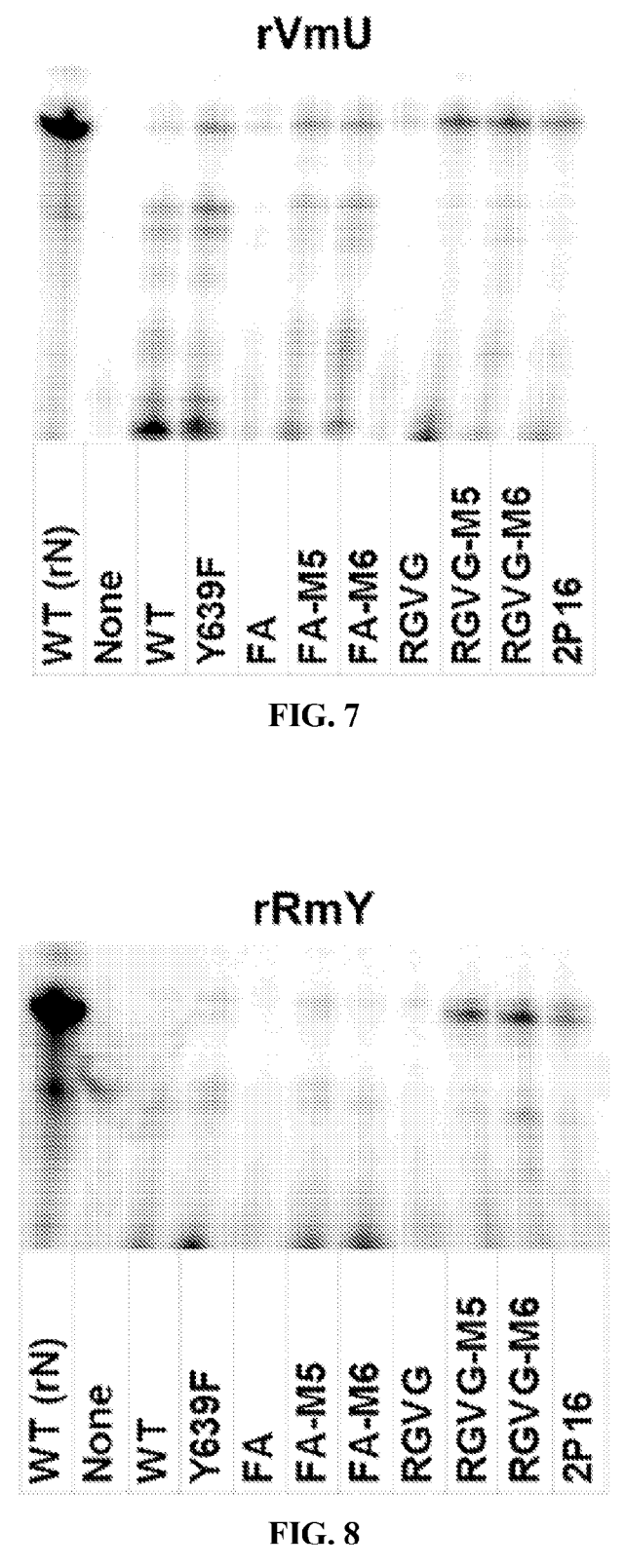
Figure 9:
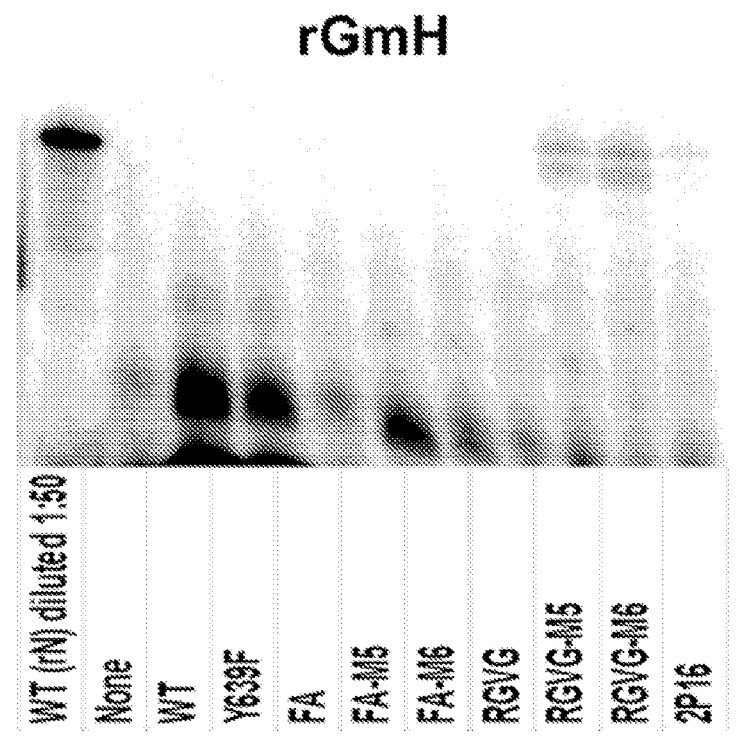
Figure 10:
FIG. 10. RGVG-M6 transcription of 2'-O-methylnucleotides (mN) is various buffers. Transcripts were analyzed by denaturing PAGE and imaged after staining in SYBR-Gold. Transcriptions ran 20 hours. A reaction containing RGVG-M6 with ribonucleotides (rN) is shown for comparison. The composition of each reaction is shown below.

End point transcription reactions contained 40 mM Tris-HCl pH 8.0, 30 mM MgCl2, 6 mM spermadine, 6 mM each NTP (or modified NTP), 10 mM DTT, 500 mM T7 RNA polymerase, 500 mM DNA template. Reactions were incubated for up to 4 or 20 hours at 37° C. DNA templates were made as above. rVmU reactions (FIG. 3C, FIG. 4A, and FIG. 7) and rRmY reaction (FIG. 4B and FIG. 8) were run four hours, labelled by inclusion of 0.17 µM (α32P)ATP (3000 Ci/mMol,) and analyzed by denaturing PAGE. rGmH reactions (FIG. 4C and FIG. 9) were run twenty hours, labelled by inclusion of 0.17 µM (α32P)GTP (3000 Ci/mMol,) and analyzed by denaturing PAGE. RGVG-M6 reactions (FIG. 5) were run twenty hours, incubated for 1 hour 37° C. with 0.03 U/ul Baseline-ZERO DNase in its supplied buffer, analyzed by denaturing PAGE and imaged after staining in SYBR-Gold. The buffer comparison (FIG. 10) used the buffers listed in the figure, was run twenty hours, incubated for 1 hour 37° C. with 0.03 U/ul Baseline-ZERO DNase in its supplied buffer, analyzed by denaturing PAGE and imaged after staining in SYBR-Gold.

mN in the permissive buffer (FIG. 6) contained 200 mM HEPES pH 7.5, 5.5 mM MgCl2, 2 mM spermidine, 0.5 mM each 2'-O-methyl-NTP, 40 mM DTT, 0.01% Triton, 10% PEG8000, 1.5 mM MnCl2, 10 U/ml YIPP, 200 nM RNA polymerase, and 200 nM DNA. Reactions were run twenty hours, incubated for 1 hour 37° C. with 0.03 U/ul Baseline-ZERO DNase in its supplied buffer, analyzed by denaturing PAGE and imaged after staining in SYBR-Gold.

32P gels were exposed to a storage phosphor screen (Molecular Dynamics) before imaging on a STORM 840 Phospoimager (GE Healthcare). Autoradiographs were analyzed using ImageQuant (GE Healthcare).

Thermal Melt Measurements

The relative thermal stability of each T7 RNA polymerase was assessed by incubating 0.5 mg/ml enzyme in PBS buffer with TexasRed dye (Invitrogen). Enzyme/dye mixtures were equilibrated at 37° C. for 10 minutes and heated at a rate of 0.07° C./s to 97° C. using a LightCycler 96 thermocycler, while fluorescence was monitored (Excitation 577 nm/Emission 620 nm). The first derivatives of the change in fluorescence as a function of time were used to approximate the relative $T_m$. Data were analysed using Roche thermocycler software.

Example 2

Stabilizing Mutations Increase the Activity of the T7 RNA Polymerase Mutant G542V H784S Previous experiments selecting for RNA polymerases with altered substrate specificity (Chelliserrykattil & Ellington, 2004) focused on the four amino acids that are proximal to the incoming nucleotide (Cheetham, 1999; Temiakov, et al., 2004), and thus likely played a role in substrate recognition. One of the resulting mutants, called "VRS," could incorporate 2'F-modified pyrimidines. VRS had mutations at two of the randomized residues (ie G542V and H784S). Interestingly, an H772R mutation also arose during the selection, despite H772 not being randomized. H772R is not near the substrate recognition domain, but has been seen in other selections for T7 RNA polymerase activity (Ellefson, et al., 2013; Dickinson, et al., 2013). To test whether H772R is a general stabilizing mutation, a derivative of VRS without H772R, termed "VS," was constructed. Purified enzymes were tested for their ability to polymerase RNA composed either of natural NTPs (rN) or of ribo-purines and 2'-F-pyrimidines (rRfY; FIG. 1). Real-time polymerase activity was assayed using the fluorescent aptamer spinach in the presence of DFHBI (Van Nies et al., 2013). Spinach will bind DFHBI and fluoresce irrespective of whether it is transcribed as a purely ribo-aptamer or when substituted with 2'-F-pyrimidines, although the 2'-F-pyrimidine version is only about 30% as fluorescent as the purely ribonucleotide version. 2'-O-methyl substituted spinach is not detectably fluorescent.

Notably, VS showed a decrease in activity for each substrate composition. This suggests that H772R contributes to the overall activity of VRS, apart from any substrate preference considerations. Several more derivatives of VRS with additional mutations were created and tested for their ability to increase the activity of VRS. The so-called "M5" (S430P, N433T, S633P, F849I, and F880Y; (U.S. Pat. No. 7,507,567) and "M6" (M5 with the additional P266L mutation, associated with promoter clearance (Guillerez, et al., 2005) sets of mutations increased activity of the VRS mutant, both for rN and rRfY incorporation.

Example 3

Figures 2A, 2B:
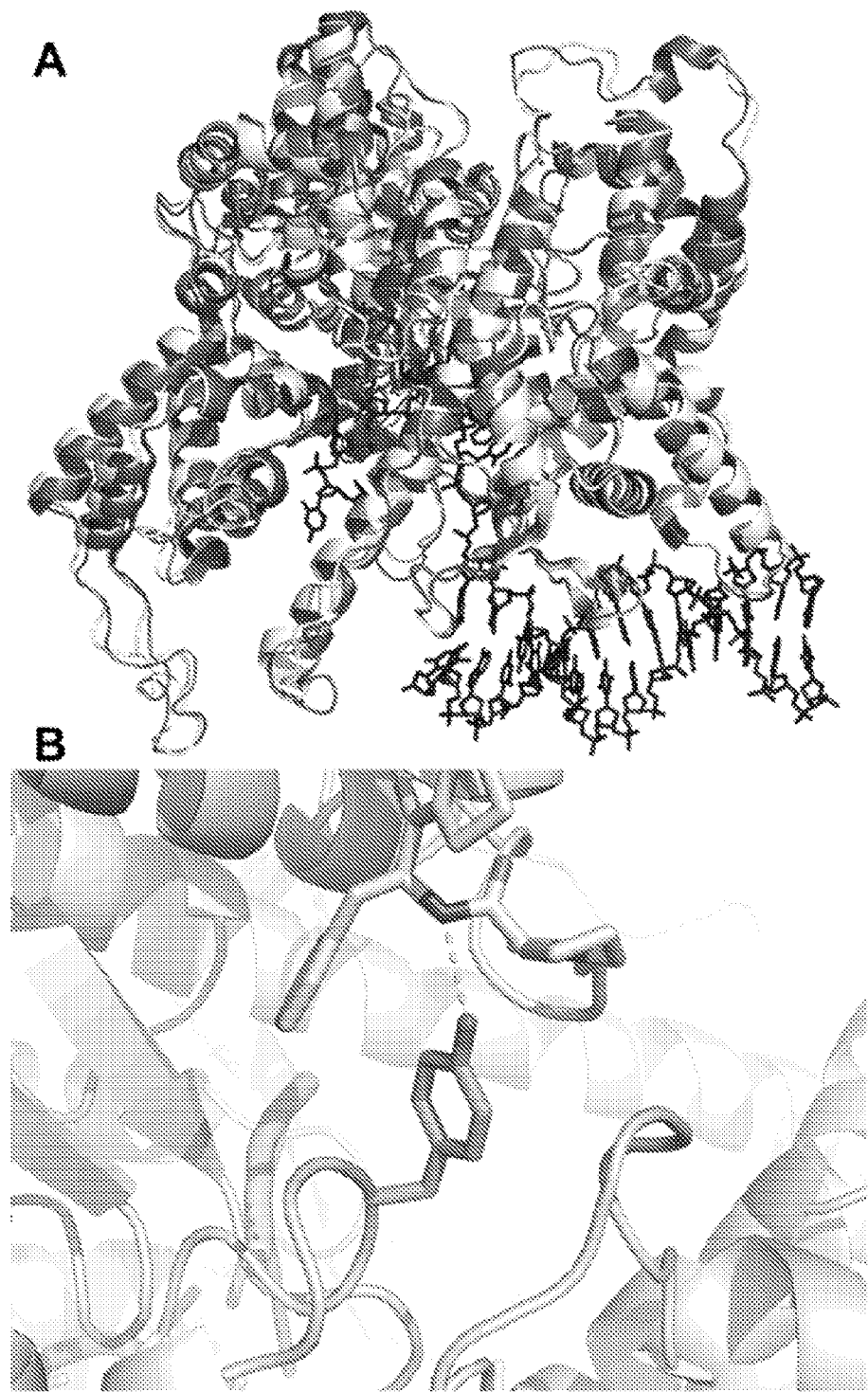
FIGS. 2A-2B. Structure of the transcribing thermostable "M5" RNA polymerase initiation complex. A) The M5 T7 RNA polymerase (white) overlayed with the wildtype T7 RNA polymerase (dark gray, PDB accession number 1QLN (Cheetham, 1999)). B) The added hydroxyl group resulting from the F880Y mutation forms a hydrogen bond (dashed line) with the peptide backbone between P474 and F475.

The "M5" Mutations Increase the Activity of Several T7 RNA Polymerase Substrate Specificity Mutants The "M5" mutations arose in a T7 RNA polymerase selection for transcriptional activity at higher temperatures. In a wild type background, these mutations increase the half-life of enzyme at 50'C and allow for transcription at that temperature. The M5 protein was crystalized, and few gross morphological differences to the wild-type T7 RNA polymerase crystal (Cheetham, 1999) are apparent (FIG. 2A). There is, however, an added hydrogen bond made by F880Y, which may stabilize the two halves of the palm domain (FIG. 2B). It should be noted that the F880Y mutation is not sufficient to increase VRS activity (see VRSY in FIGS. 1C-1D).

It was then tested whether the M5 and M6 mutations could increase the activity of other T7 RNA polymerase mutants. Several known polymerases with altered ribose specificity namely WT, Y639F, FA, RGVG, VRS, and R425C (Table 1) were tested. To each of these specificity mutants was added a set of stability mutations, namely "L" (P266L), M5, and M6. Also included was a recently described mutant, 2P16, which is likely a stabilized version of RGVG. These 25 polymerases were purified and assayed for transcriptional activity in vitro (FIG. 3).

TABLE 1

List of T7 RNA polymerase mutants

| Enzyme | Sequence |
| --- | --- |
| WT | WT T7 RNAP |
| VS | G542V, H784S |
| VRS | G542V, H772R, H784S |
| VRS-L | P266L, G542V, H772R, H784S |
| VLRS | G542V, V625L, H772R, H784S |
| VRIS | G542V, H772R, V783I, H784S |
| VLRIS | G542V, V625L, H772R, V783I, H784S |
| VRSY | G542V, H772R, H784S, F880Y |
| VRS-M5 | S430P, N433T, G542V, S633P, H772R, H784S, F849I, F880Y |
| VRS-M6 | P266L, S430P, N433T, G542V, S633P, H772R, H784S, F849I, F880Y |
| M5 | S430P, N433T, S633P, F849I, F880Y |
| L | P266L |
| M6 | P266L, S430P, N433T, S633P, F849I, F880Y |
| Y639F | Y639F |
| Y639F-M5 | S430P, N433T, S633P, Y639F, F849I, F880Y |
| Y639F-L | P266L, Y639F |
| Y639F-M6 | P266L, S430P, N433T, S633P, Y639F, F849I, F880Y |
| FA | Y639F, H784A |
| FA-M5 | S430P, N433T, S633P, Y639F, H784A, F849I, F880Y |
| FA-L | P266L, Y639F, H784A |
| FA-M6 | P266L, S430P, N433T, S633P, Y639F, H784A, F849I, F880Y |
| R425C | R425C |
| R425C-M5 | R425C, S430P, N433T, S633P, F849I, F880Y |
| R425C-L | P266L, R425C |
| R425C-M6 | P266L, R425C, S430P, N433T, S633P, F849I, F880Y |
| RGVG | E593G, Y639V, Y685A, H784G |
| RGVG-M5 | S430P, N433T, E593G, S633P, Y639V, V685A, H784G, F849I, F880Y |
| RGVG-L | P266L, E593G, Y639V, Y685A, H784G |
| RGVG-M6 | P266L, S430P, N433T, E593G, S633P, Y639V, V685A, H784G, F849I, F880Y |
| 2P16 | I119V, G225S, K333N, D366N, F400L, E593G, Y639V, S661G, V685A, H784G, F880Y |

Figures 3A, 3B:
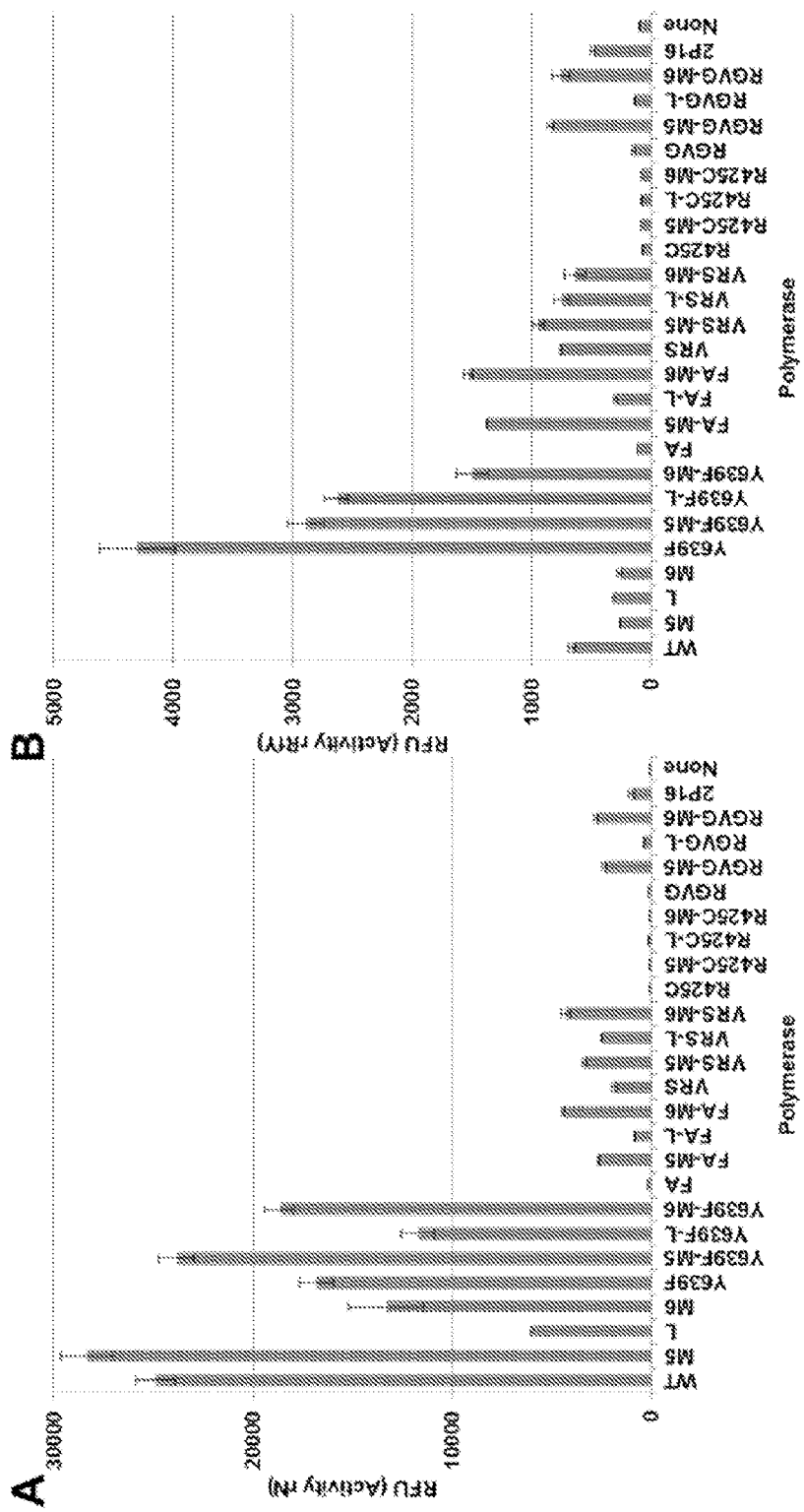
FIGS. 3A-3C. Stabilizing mutations increase the activity of the several T7 RNA polymerase substrate specificity mutants. A) Measurement of ribonucleotide (rN) transcriptional output after one hours. B) Measurement of 2'-fluoropyrimidine (rRfY) transcriptional output after two hours. Fluorescent readings (in Relative Fluorescent Units, RFU) indicate the presence of the fluorescent aptamer, spinach. Error bars represent standard error resulting from 3 independently assembled reactions. C) Transcription assay for incorporation of 2'-O-methyluridine (rVmU). Transcripts were labelled by inclusion of ($\alpha^{32}$P)ATP and analyzed by denaturing PAGE. A reaction of WT T7 RNA polymerase with ribonucleotides (rN) is included for comparison. Transcriptions ran four hours, two distinct gels are shown.
Figure 3C:
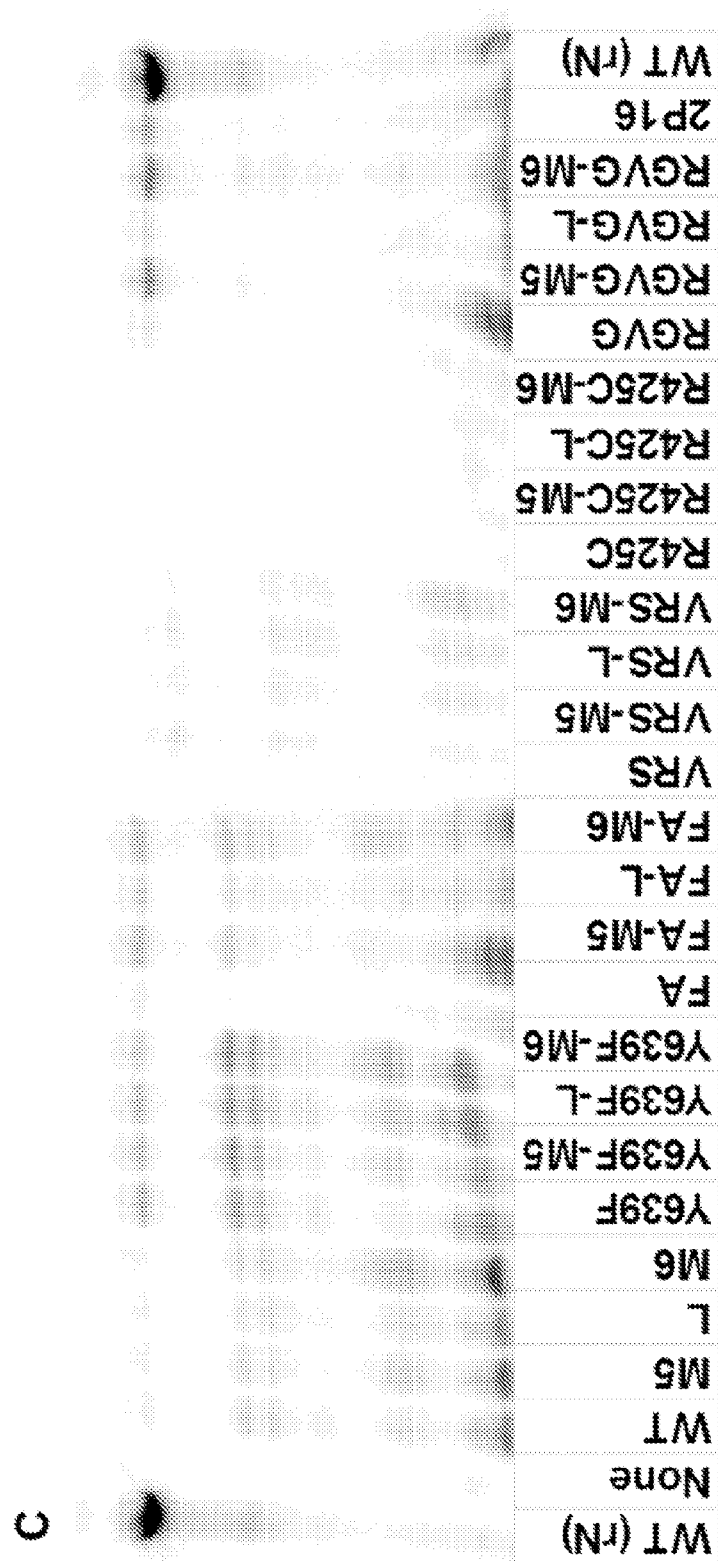

Whether transcribing natural ribotides (rN; FIG. 3A), 2'-F-pyrimidines (rRfY; FIG. 3B), or 2'-O-methyluridine (rVmU; FIG. 3C) the M5 and M6 mutations increased activity of the mutants FA, RGVG, and VRS. WT and Y639F activity on rN was slightly increased by the M5 mutations, but this trend did not hold up with rRfY or rVmU incorporation. It is evident that the 2P16 is indeed more active than RGVG (as previously reported (Siegmund, et al., 2012)) but is not as active as either RGVG M5 or RGVG M6. No transcription was detected from the R425C family of polymerases.

A subset of the most active polymerases were assayed for the ability to incorporate 2'-O-methyluridine (rVmU), 2'-O-methylpyrimidines (rRmY), and 2'-O-methyladenosine and 2'-O-methylpyrimidines (rGmH) (FIG. 4, FIGS. 7-9). As was case for rN and rRfY above, the M5 mutations enhanced the activity of the FA and RGVG enzymes for each set of substrates. RGVG-M6 was the most active enzyme in all conditions, yielding at least 25-fold more RNA than the FA mutant, which is the most commonly used enzyme for generating 2'-O-methyl RNA.

Figure 11:
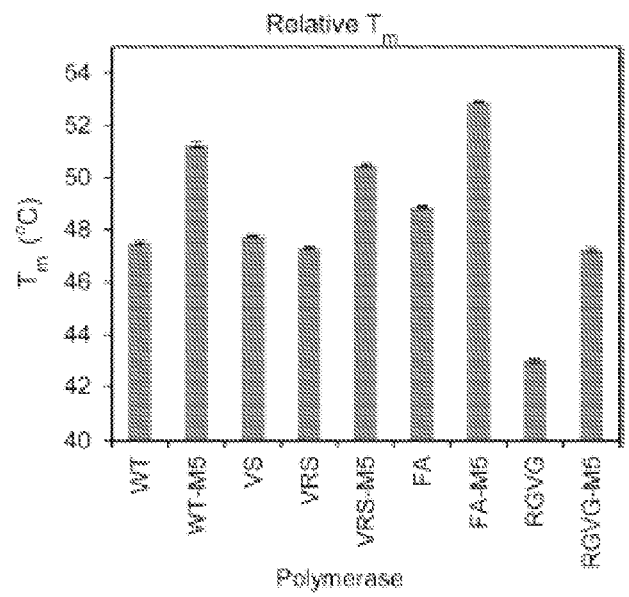
FIG. 11. The relative thermal stability of each T7 RNA polymerase mutant. Thermal melt assays were performed for several mutants T7 RNA polymerase. First derivatives of the change in fluorescence as a function of time were used to approximate the relative $T_m$. Data shown are the average of three independently assembled reactions with error bars representing standard error.
Figure 12:
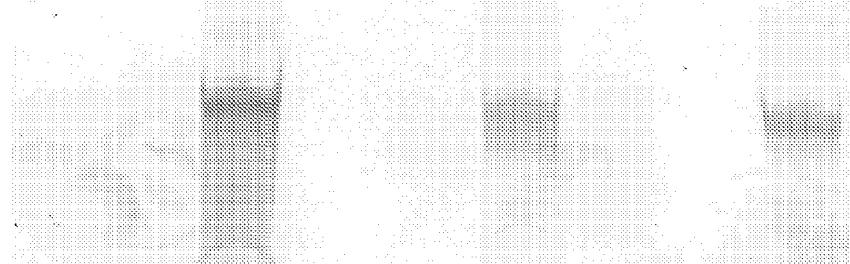
FIG. 12. Comparison of RGVG-M5 and RGVG-M6 to Y639L H784A in the transcription of 2'-O-methylnucleotides (mN) in permissive buffer. Transcripts were analyzed by denaturing PAGE and imaged after staining in SYBR-Gold. Transcriptions ran 20 hours. A reaction containing WT T7 RNA polymerase with ribonucleotides (rN) is shown for comparison.

Thermal-melt assays confirmed that, for all T7 RNA polymerase variants tested, addition of the M5 mutations increased their thermal stability (FIG. 11). The weakly active RGVG mutant has a $T_m$ almost 5° C. lower than that of WT T7 RNA polymerase, but this loss of stability and RGVG's activity are rescued by the M5 mutations. Contrary to expectations, however, the similarly weak VRS and FA mutants do not have low melting temperatures, and the H772R mutation did not have the expected effect on $T_m$. It seems that the increase in activity due to the addition of these mutations cannot be solely attributed to an increase of stability.

Example 4

Figure 5:
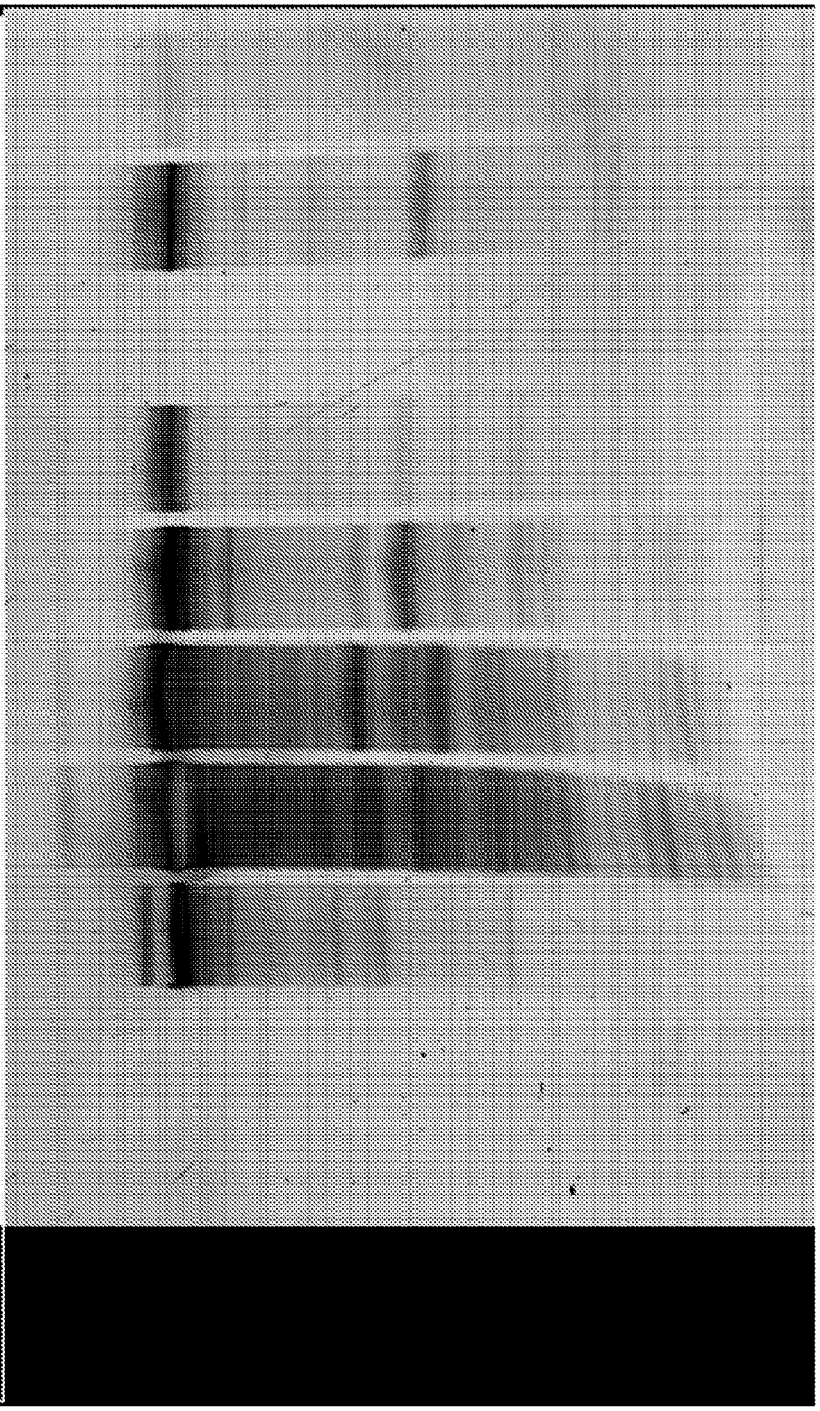
FIG. 5. RGVG M6 can transcribe fully-modified RNA. Transcription assay for RGVG-M6 catalyzed incorporation of ribonucleotides (rN); 2'-O-methyluridine (rVmU); 2'-O-methylpyrimidines (rRmY); 2'-O-methyladenosine and 2'-O-methylpyrimidines (rGmH); 2'-O-methylnucleotides (mN); 2'-fluoro-purines and 2'-O-methylpyrimidines (fRmY); and 2'-fluoro-guanosine, 2'-O-methyladenosine, and 2'-O-methylpyrimidines (fGmH). Transcripts were analyzed by denaturing PAGE and imaged after staining in SYBR-Gold. Transcriptions ran 20 hours. A reaction (10-fold diluted) containing WT T7 RNA polymerase with ribonucleotides (rN) is shown for comparison.

T7 RNA Polymerase R6 is Effective for High-Yield Transcription of Fully Modified RNA After demonstrating that RGVG-M6 could catalyse the formation of RNA containing three 2'-O-methylnucleotides, its ability to generate fully-modified RNA was assayed. RGVG-M6 was able to polymerase using a combination 2'-F-purines and 2'-O-methylpyrimidines (fRmY) as well as a combination of 2'-F-guanosine, 2'-O-methyladenosine, and 2'-O-methylpyrimidines (fGmH) (FIG. 5). Fully 2'-O-methyl RNA (mN) was not obtained.

Previous reports of mN incorporation have used more permissive buffer compositions, including manganese as well as rGMP and/or rGTP. RGVG-M6's ability to synthesize mN RNA in several such permissive buffers was tested (FIG. 10) and it was determined that effective mN polymerization was achieved in buffers that included rGMP or rGTP. A panel of enzymes for mN polymerization in this permissive buffer (200 mM HEPES pH 7.5, 5.5 mM MgCl$_2$, 2 mM spermidine, 0.5 mM each 2'-O-methyl-NTP, 40 mM DTT, 0.01% Triton, 10% PEG8000, 1.5 mM MnCl$_2$, 10 U/ml yeast inorganic pyrophosphatase, 200 nM RNA polymerase, and 200 nM DNA) was tested. FA-M5 and FA-M6 show an increase in activity relative to the parental FA mutant. RGVG-M5, RGVG-M6, and 2P16 showed a marked improvement over the parental RGVG. In addition, RGVG-M5 and RGVG-M6 generate substantially more RNA in this buffer than the Y639L H784A mutant (U.S. Pat. No. 8,105,813).

Although certain embodiments have been described above with a certain degree of particularity, or with reference to one or more individual embodiments, those skilled in the art could make numerous alterations to the disclosed embodiments without departing from the scope of this invention. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not to be interpreted as including means-plus- or step-plus-function limitations, unless such a limitation is explicitly recited in a given claim using the phrase(s) "means for" or "step for," respectively.

REFERENCES

The following references, to the extent that they provide exemplary procedural or other details supplementary to those set forth herein, are specifically incorporated herein by reference.
U.S. Pat. No. 7,507,567
U.S. Pat. No. 8,105,813
Beaudry, et al., *Chem Biol.* 7:323-34, 2000.
Brieba & Sousa, *Biochemistry.* 39:919-23, 2000.
Bryksin & Matsumura, *Biotechniques.* 48:463-5, 2010.
Burmeister, et al., *Chem Biol.* 12:25-33, 2005.
Cheetham & Steitz, *Science.* 286:2305-2309, 1999.
Chelliserrykattil & Ellington, *Nat Biotechnol.* 22:1155-60, 2004.
Dean & Bennett, *Oncogene.* 22:9087-96, 2003.
Dickinson, et al., *Proc Natl Acad Sci USA.* 32(1):97-101, 2013.
Ellefson, *Nat Biotechnol.* 32(1):97-101, 2014.
Ellington & Szostak, *Nature.* 346:818-822, 1990.
Gibson, *Methods Enzymol.* 498:349-61, 2011.
Guillerez, et al., *Proc Natl Acad Sci USA.* 102(17):5958-63, 2005.
Healy, et al., *Pharm Res.* 21:2234-46, 2004.
Huang, et al., *Biochemistry.* 36:8231-42, 1997.
Ibach, *J Biotechnol.* 167:287-95, 2013.
Jackson, et al., *RNA.* 12(7):1197-205, 2006.
Keefe & Cload, *Curr Opin Chem Biol.* 12: 448-56, 2008.
Knudsen, et al., *Curr Protoc Nucleic Acid Chem*. Chapter 9, Unit 9.6, 2002.
Kostyuk, et al., *FEBS Lett.* 369:165-8, 1995.
Kraynack & Baker, *RNA.* 12(1):163-76, 2006.
Layzer, *RNA.* 10:766-771, 2004.
Lupold, et al., *Cancer Res.* 62(14):4029-33, 2002.
Majlessi, et al., *Nucleic Acids Res.* 26:2224-9, 1998.
Padilla & Sousa, *Nucleic Acids Res.* 30:e138, 2002.
Romero & Arnold, *Nat Rev Mol Cell Biol.* 10:866-76, 2009.
Siegmund, et al., *Chem Commun. (Camb)*, 48:9870-2, 2012.
Sousa & Padilla, *EMBO J.* 14:4609-21, 1995.
Temiakov, et al., *Cell.* 116:381-91, 2004.
Van Nies, et al. *ChemBioChem* 14:1963-66, 2013.
Wang, et al., *J Mol Biol.* 320:85-95, 2002.
Waters, et al., *Blood.* 117:5514-22, 2011.
Wilson & Keefe, *Curr Opin Chem Biol.* 10:607-14, 2006.

The invention claimed is:

1. A T7 RNA polymerase variant comprising:
   a) one or more substrate-broadening amino acid substitutions that confer an enhanced ability to incorporate 2'-modified mononucleotides compared to a wild-type T7 RNA polymerase, wherein the substrate-broadening amino acid substitutions comprise one of the following sets of substitutions relative to SEQ ID NO: 1:
      i) G542V, H772R, and H784S;
      ii) Y639F and H784A; or
      iii) E593G, Y639V, V685A, and H784G; and
   b) one or more activity-enhancing amino acid substitutions that increase the transcriptional activity of the T7 polymerase variant relative to T7 polymerase variants without the activity-enhancing amino acid substitutions, wherein the activity-enhancing amino acid substitutions comprise one of the following sets of substitutions relative to SEQ ID NO: 1:
      i) S430P, N433T, S633P, F849I, and F880Y; and
      ii) P266L, S430P, N433T, S633P, F849I, and F880Y.

2. The T7 RNA polymerase variant of claim 1, wherein the 2'-modified mononucleotides comprise one or more of 2'-fluoro CTP, 2'-fluoro UTP, 2'-fluoro ATP, 2'-fluoro GTP, 2'-amino CTP, 2'-amino UTP, 2'-amino ATP, 2'-O-methyl UTP, 2'-O-methyl ATP, 2'-O-methyl CTP, and 2'-O-methyl GTP.

3. A T7 RNA polymerase variant comprising the following amino acid substitutions: N433T, E593G, Y639V, V685A, H784G, S430P, S633P, F849I, and F880Y.

4. A nucleic acid molecule encoding the T7 RNA polymerase variant of claim 1.

5. An expression vector comprising the nucleic acid molecule of claim 4.

6. An isolated cell transformed with the expression vector of claim 5, wherein the transformed cell is capable of expressing the T7 RNA polymerase variant.

7. A reaction mixture comprising the T7 RNA polymerase variant of claim 1, a DNA template comprising a T7 RNA polymerase promoter, and one or more 2'-modified mononucleotides.

8. The reaction mixture of claim 7, wherein the one or more 2'-modified mononucleotides comprise one or more of 2'-fluoro CTP, 2'-fluoro UTP, 2'-fluoro ATP, 2'-fluoro GTP, 2'-amino CTP, 2'-amino UTP, 2'-amino ATP, 2'-O-methyl UTP, 2'-O-methyl ATP, 2'-O-methyl CTP, and 2'-O-methyl GTP.

9. A method of making an RNA polynucleotide comprising one or more 2'-modified mononucleotides, the method comprising incubating the reaction mixture of claim 7 at 37° C., wherein the RNA polynucleotide is a nuclease-resistant aptamer.

10. A method of making a therapeutic RNA polynucleotide comprising one or more 2'-modified mononucleotides, the method comprising incubating the reaction mixture of claim 7 at 37° C., wherein the DNA template further comprises a template sequence complementary to the therapeutic RNA polynucleotide, and wherein the therapeutic RNA polynucleotide is an miRNA, a pre-miRNA, or an aptamer.

11. The method of claim 10, wherein the one or more 2'-modified mononucleotides comprises one or more of 2'-fluoro CTP, 2'-fluoro UTP, 2'-fluoro ATP, and 2'-fluoro GTP.

12. The method of claim 10, wherein the nucleotide sequence of the therapeutic RNA polynucleotide is complementary to a portion of the sequence of a target gene mRNA.

13. The method of claim 12, wherein the one or more 2' modified mononucleotides comprises one or more of 2'-O-methyl UTP, 2'-O-methyl ATP, 2'-O-methyl GTP, and 2'-O-methyl CTP.

14. A method of making an RNA polynucleotide probe comprising one or more 2'-modified mononucleotides, the method comprising incubating the reaction mixture of claim 7 at 37° C., wherein the DNA template further comprises a template sequence complementary to the RNA polynucleotide probe.

15. The T7 RNA polymerase variant of claim 1, wherein the substrate-broadening amino acid substitutions comprise E593G, Y639V, V685A, and H784G and wherein the activity-enhancing amino acid substitutions comprise S430P, N433T, S633P, F849I, and F880Y, and wherein the activity enhancing amino acid substitutions further comprise P266L.

16. The T7 RNA polymerase variant of claim 1, wherein the substrate-broadening amino acid substitutions comprise E593G, Y639V, V685A, and H784G and wherein the activity-enhancing amino acid substitutions comprise S430P, N433T, S633P, F849I, and F880Y, and wherein the T7 RNA polymerase variant is capable of incorporating 2'-O-methyl UTP and 2'-O-methyl CTP into RNA.

17. The T7 RNA polymerase variant of claim 16, wherein the T7 RNA polymerase variant is further capable of incorporating 2'-O-methyl ATP and 2'-O-methyl GTP into RNA.

18. The T7 RNA polymerase variant of claim 1, wherein the substrate-broadening amino acid substitutions comprise E593G, Y639V, V685A, and H784G and wherein the activity-enhancing amino acid substitutions comprise S430P, N433T, S633P, F849I, and F880Y, and wherein the T7 RNA polymerase variant is capable of incorporating 2'-O-methyl UTP, 2'-O-methyl CTP, 2'-O-methyl ATP, and 2'-O-methyl GTP into RNA in a single reaction mixture.

19. The reaction mixture of claim 1, wherein the one or more 2'-modified mononucleotides comprise 2'-O-methyl UTP, 2'-O-methyl ATP, 2'-O-methyl CTP, and 2'-O-methyl GTP.

* * * * *